(12) United States Patent
Eisen et al.

(10) Patent No.: US 11,752,006 B2
(45) Date of Patent: Sep. 12, 2023

(54) ANGULARLY ADJUSTABLE INTERVERTEBRAL CAGES WITH INTEGRATED RATCHET ASSEMBLY

(71) Applicant: EIT Emerging Implant Technologies GmbH, Wurmlingen (DE)

(72) Inventors: Guntmar Eisen, Wurmlingen (DE); Detlev Ganter, Wurmlingen (DE); Stephan Geiger, Wurmlingen (DE)

(73) Assignee: EIT Emerging Implant Technologies GmbH

( * ) Notice: Subject to any disclaimer, the term of this patent is extended or adjusted under 35 U.S.C. 154(b) by 259 days.

(21) Appl. No.: 17/106,233

(22) Filed: Nov. 30, 2020

(65) Prior Publication Data
US 2021/0093463 A1   Apr. 1, 2021

Related U.S. Application Data

(63) Continuation of application No. 16/293,374, filed on Mar. 5, 2019, now Pat. No. 10,881,524.
(Continued)

(51) Int. Cl.
*A61F 2/44* (2006.01)
*A61F 2/46* (2006.01)
(Continued)

(52) U.S. Cl.
CPC ............ *A61F 2/4425* (2013.01); *A61F 2/447* (2013.01); *A61F 2/4455* (2013.01);
(Continued)

(58) Field of Classification Search
CPC .................. A61F 2/4425; A61F 2002/443
See application file for complete search history.

(56) References Cited

U.S. PATENT DOCUMENTS 6,685,742 B1 * 2/2004 Jackson ............... A61F 2/447
623/17.11
9,283,084 B1   3/2016 O'Hara
(Continued)

FOREIGN PATENT DOCUMENTS

CN    105769392 A    7/2016
CN    107224341 A    10/2017
(Continued)

*Primary Examiner* — Christian A Sevilla
(74) *Attorney, Agent, or Firm* — BakerHostetler

(57) ABSTRACT

The embodiments provide various interbody fusion spacers, or cages, for insertion between adjacent vertebrae. The cages may have integrated ratchet assemblies that allow the cage to change size and angle as needed, with little effort. The cages may have a first, insertion configuration characterized by a reduced size to facilitate insertion through a narrow access passage and into the intervertebral space. The cages may be inserted in a first, reduced size and then expanded to a second, larger size once implanted. In their second configuration, the cages are able to maintain the proper disc height and stabilize the spine by restoring sagittal balance and alignment. Additionally, the intervertebral cages are configured to be able to adjust the angle of lordosis, and can accommodate larger lordotic angles in their second, expanded configuration. Further, these cages may promote fusion to further enhance spine stability by immobilizing the adjacent vertebral bodies.

15 Claims, 9 Drawing Sheets

Related U.S. Application Data

(60) Provisional application No. 62/639,282, filed on Mar. 6, 2018.

(51) Int. Cl.
   *A61F 2/30* (2006.01)
   *A61F 2/28* (2006.01)

(52) U.S. Cl.
   CPC ..... *A61F 2/4611* (2013.01); *A61F 2002/2835* (2013.01); *A61F 2002/3054* (2013.01); *A61F 2002/30069* (2013.01); *A61F 2002/30161* (2013.01); *A61F 2002/30205* (2013.01); *A61F 2002/30261* (2013.01); *A61F 2002/30266* (2013.01); *A61F 2002/30322* (2013.01); *A61F 2002/30471* (2013.01); *A61F 2002/30556* (2013.01); *A61F 2002/30579* (2013.01); *A61F 2002/30784* (2013.01); *A61F 2002/30985* (2013.01)

(56) References Cited

U.S. PATENT DOCUMENTS

| | | | |
|---|---|---|---|
| 2002/0128713 A1* | 9/2002 | Ferree | A61F 2/4465 623/17.11 |
| 2002/0143401 A1* | 10/2002 | Michelson | A61F 2/446 623/17.16 |
| 2005/0049590 A1 | 3/2005 | Alleyne et al. | |
| 2010/0185291 A1 | 7/2010 | Jimenez et al. | |
| 2011/0046682 A1 | 2/2011 | Stephan et al. | |
| 2012/0226357 A1* | 9/2012 | Varela | A61F 2/447 623/17.16 |
| 2012/0265309 A1 | 10/2012 | Glerum et al. | |
| 2013/0023994 A1* | 1/2013 | Glerum | A61F 2/447 623/17.16 |
| 2013/0060278 A1 | 3/2013 | Bozung et al. | |
| 2013/0197648 A1 | 8/2013 | Boehm et al. | |
| 2014/0094918 A1 | 4/2014 | Vishnubholta et al. | |
| 2014/0121774 A1 | 5/2014 | Glerum et al. | |
| 2014/0128977 A1 | 5/2014 | Glerum et al. | |
| 2014/0249630 A1 | 9/2014 | Weiman | |
| 2014/0343678 A1 | 11/2014 | Suddaby et al. | |
| 2015/0012097 A1 | 1/2015 | Ibarra et al. | |
| 2015/0374509 A1 | 12/2015 | McLean | |
| 2016/0015522 A1 | 1/2016 | Arnin | |
| 2016/0022438 A1* | 1/2016 | Lamborne | A61F 2/447 623/17.16 |
| 2016/0166396 A1 | 6/2016 | McClintock | |
| 2016/0361176 A1 | 12/2016 | Weiman et al. | |
| 2017/0216045 A1 | 8/2017 | Dewey et al. | |
| 2017/0367845 A1* | 12/2017 | Eisen | A61F 2/4611 |
| 2018/0064551 A1* | 3/2018 | Stein | A61F 2/447 |
| 2018/0116815 A1 | 5/2018 | Kuyler et al. | |
| 2018/0289499 A1 | 10/2018 | Robinson | |
| 2019/0021868 A1 | 1/2019 | Ludwig et al. | |
| 2019/0110902 A1 | 4/2019 | Vigliotti et al. | |
| 2019/0254836 A1 | 8/2019 | Cowan et al. | |
| 2019/0298524 A1 | 10/2019 | Lauf et al. | |
| 2019/0388232 A1 | 12/2019 | Purcell et al. | |
| 2020/0261241 A1 | 8/2020 | Robinson | |
| 2022/0265436 A1* | 8/2022 | Suddaby | A61F 2/447 |

FOREIGN PATENT DOCUMENTS

| | | |
|---|---|---|
| JP | 2004-130077 A | 4/2004 |
| JP | 2005-523732 A | 8/2005 |
| JP | 2008-517723 A | 5/2008 |
| JP | 2016-514567 A | 5/2016 |
| WO | 2017/132537 A1 | 8/2017 |

\* cited by examiner

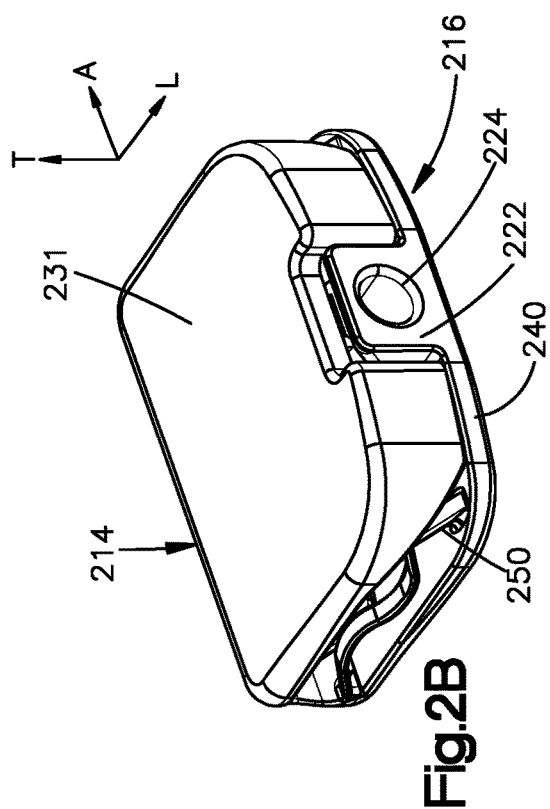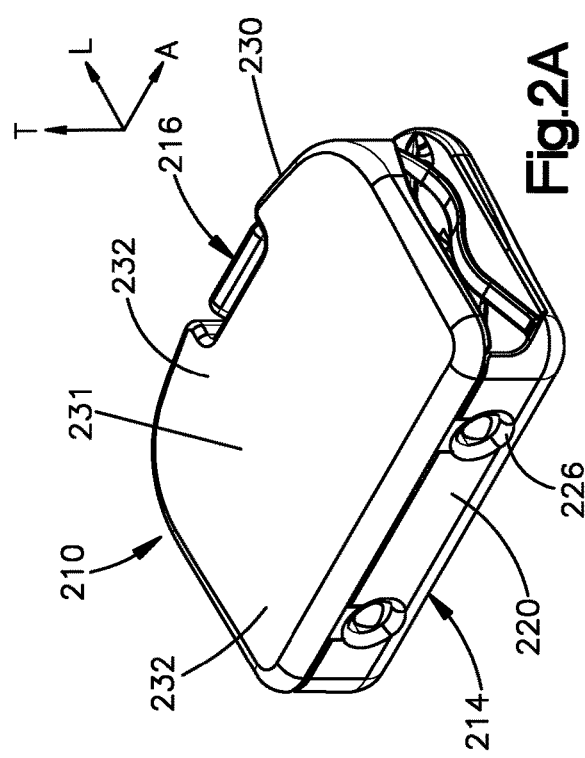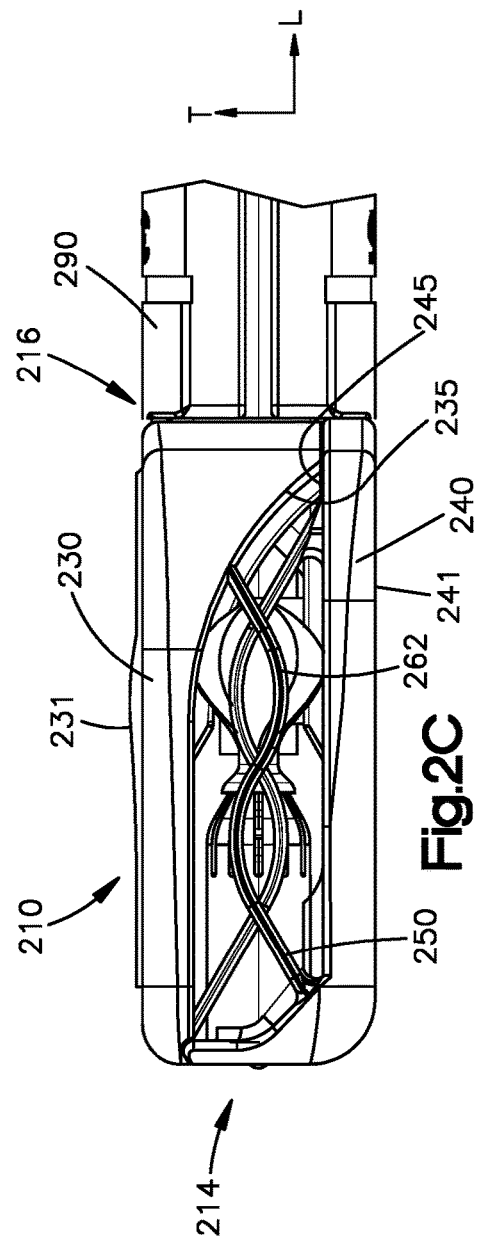

ANGULARLY ADJUSTABLE INTERVERTEBRAL CAGES WITH INTEGRATED RATCHET ASSEMBLY

CROSS-REFERENCE TO RELATED APPLICATIONS

This is a continuation of U.S. patent application Ser. No. 16/293,374 filed Mar. 5, 2019, which claims the benefit of U.S. Patent Application Ser. No. 62/639,282 filed Mar. 6, 2018, the disclosure of each of which is hereby incorporated by reference as if set forth in its entirety herein.

TECHNICAL FIELD

The present disclosure relates to implantable orthopedic devices, and more particularly to implantable devices for stabilizing the spine. Even more particularly, the present disclosure relates to angularly adjustable intervertebral cages comprising integrated ratchet assemblies that allow expansion of the cages from a first, insertion configuration having a reduced size to a second, implanted configuration having an expanded size. The intervertebral cages are configured to adjust and adapt to lordotic angles, particularly larger lordotic angles, while restoring sagittal balance and alignment of the spine.

BACKGROUND

The use of fusion-promoting interbody implantable devices, often referred to as cages or spacers, is well known as the standard of care for the treatment of certain spinal disorders or diseases. For example, in one type of spinal disorder, the intervertebral disc has deteriorated or become damaged due to acute injury or trauma, disc disease or simply the natural aging process. A healthy intervertebral disc serves to stabilize the spine and distribute forces between vertebrae, as well as cushion the vertebral bodies. A weakened or damaged disc therefore results in an imbalance of forces and instability of the spine, resulting in discomfort and pain. The standard treatment today may involve surgical removal of a portion, or all, of the diseased or damaged intervertebral disc in a process known as a partial or total discectomy, respectively. The discectomy is often followed by the insertion of a cage or spacer to stabilize this weakened or damaged spinal region. This cage or spacer serves to reduce or inhibit mobility in the treated area, in order to avoid further progression of the damage and/or to reduce or alleviate pain caused by the damage or injury. Moreover, these types of cages or spacers serve as mechanical or structural scaffolds to restore and maintain normal disc height, and in some cases, can also promote bony fusion between the adjacent vertebrae.

However, one of the current challenges of these types of procedures is the very limited working space afforded the surgeon to manipulate and insert the cage into the intervertebral area to be treated. Access to the intervertebral space requires navigation around retracted adjacent vessels and tissues such as the aorta, vena cava, dura and nerve roots, leaving a very narrow pathway for access. The opening to the intradiscal space itself is also relatively small. Hence, there are physical limitations on the actual size of the cage that can be inserted without significantly disrupting the surrounding tissue or the vertebral bodies themselves.

Further complicating the issue is the fact that the vertebral bodies are not positioned parallel to one another in a normal spine. There is a natural curvature to the spine due to the angular relationship of the vertebral bodies relative to one another. The ideal cage must be able to accommodate this angular relationship of the vertebral bodies, or else the cage will not sit properly when inside the intervertebral space. An improperly fitted cage would either become dislodged or migrate out of position, and lose effectiveness over time, or worse, further damage the already weakened area.

Thus, it is desirable to provide intervertebral cages or spacers that not only have the mechanical strength or structural integrity to restore disc height or vertebral alignment to the spinal segment to be treated, but also be configured to easily pass through the narrow access pathway into the intervertebral space, and then accommodate the angular constraints of this space, particularly for larger lordotic angles.

BRIEF SUMMARY

The present disclosure includes spinal implantable devices that address the aforementioned challenges and meet the desired objectives. These spinal implantable devices, or more specifically intervertebral cages or spacers, are configured to be expandable as well as angularly adjustable. The cages can include upper and lower plates for bearing against endplates of the vertebral bodies, and have integrated ratchet assemblies that allow the cage to change size and angle as needed, with little effort. In some embodiments, the cages may have a first or insertion configuration characterized by a first height to facilitate insertion through a narrow access passage and into the intervertebral space. The cages may be inserted in the first or insertion configuration, and then expanded to a second expanded configuration characterized by a second height that is greater than the first height. In the second or expanded configuration, the cages are able to maintain the proper disc height and stabilize the spine by restoring sagittal balance and alignment. Additionally, the intervertebral cages are configured to be angularly adjustable to correspond to an angle of lordosis, and can accommodate larger lordotic angles in their second, expanded configuration. Further, the cages can promote fusion to further enhance spine stability by immobilizing the adjacent vertebral bodies.

According to one aspect of the disclosure, the cages may be manufactured using selective laser melting (SLM) techniques, a form of additive manufacturing. The cages may also be manufactured by other comparable techniques, such as for example, 3D printing, electron beam melting (EBM), layer deposition, and rapid manufacturing. With these production techniques, it is possible to create an all-in-one, multi-component device which may have interconnected and movable parts without further need for external fixation or attachment elements to keep the components together. Accordingly, the intervertebral cages of the present disclosure are formed of multiple, interconnected parts that do not require additional external fixation elements to keep together.

Further, cages manufactured in this manner do not have connection seams whereas devices traditionally manufactured have joined seams to connect one component to another. These connection seams can often represent weakened areas of the implantable device, particularly when the bonds of these seams wear or break over time with repeated use or under stress. By manufacturing the disclosed implantable devices using additive manufacturing, one of the advantages is that connection seams are avoided entirely and therefore the problem is avoided.

Another advantage of the present devices is that, by manufacturing these devices using an additive manufacturing process, all of the components of the device (that is, both the intervertebral cage and the pins for expanding and blocking) can remain a complete construct during both the insertion process as well as the expansion process. That is, multiple components are provided together as a collective single unit so that the collective single unit is inserted into the patient, actuated to allow expansion, and then allowed to remain as a collective single unit in situ. In contrast to other cages requiring insertion of external screws or wedges for expansion, in the present embodiments the expansion and blocking components do not need to be inserted into the cage, nor removed from the cage, at any stage during the process. This is because these components are manufactured so as to be captured internally within the cages, and while freely movable within the cage, are already contained within the cage so that no additional insertion or removal is necessary.

In some embodiments, the cages can have an engineered cellular structure on a portion of, or over the entirety of, the cage. This cellular structure can include a network of pores, microstructures and nanostructures to facilitate osteosynthesis. For example, the engineered cellular structure can comprise an interconnected network of pores and other micro and nano sized structures that take on a mesh-like appearance. These engineered cellular structures can be provided by etching or blasting, to change the surface of the device on the nano level. One type of etching process may utilize, for example, HF acid treatment.

In addition, these cages can also include internal imaging markers that allow the user to properly align the device and generally facilitate insertion through visualization during navigation. The imaging marker shows up as a solid body amongst the mesh under x-ray, fluoroscopy or CT scan, for example.

Another benefit provided by the implantable devices of the present disclosure is that they can be specifically customized to the patient's needs. Customization of the implantable devices is relevant to providing a preferred modulus matching between the implant device and the various qualities and types of bone being treated, such as for example, cortical versus cancellous, apophyseal versus central, and sclerotic versus osteopenic bone, each of which has its own different compression to structural failure data. Likewise, similar data can also be generated for various implant designs, such as for example, porous versus solid, trabecular versus non-trabecular, etc. Such data may be cadaveric, or computer finite element generated. Clinical correlation with, for example, DEXA data can also allow implantable devices to be designed specifically for use with sclerotic, normal, or osteopenic bone. Thus, the ability to provide customized implantable devices such as the ones provided herein allow the matching of the Elastic Modulus of Complex Structures (EMOCS), which enable implantable devices to be engineered to minimize mismatch, mitigate subsidence and optimize healing, thereby providing better clinical outcomes.

In one exemplary embodiment, an expandable spinal implant is provided. The expandable spinal implant may comprise a housing comprising an upper plate configured for placement against an endplate of a first vertebral body and a lower plate configured for placement against an endplate of a second, adjacent vertebral body. The expandable spinal implant may further include an integrated ratchet assembly within the housing that is configured to effect angular adjustment of the spinal implant. The ratchet assembly may comprise an enlarged head attached to a shaft having a series of flanges, and a sleeve having a slotted opening for capturing the shaft. In use, release of the shaft from the sleeve enables the enlarged head to urge against the upper and lower plates and cause angular adjustment of the plates relative to one another.

In accordance to one aspect of the embodiment, the housing may include one or springs configured to control expansion of the sidewalls. The springs can be configured as deformable strips, and can extend from the upper plate to the lower plate. The upper and lower plates may connect to the housing by a cone hinge. The housing may include an instrument-engaging opening. The housing may include a porous surface on at least one of the upper and lower surfaces.

In some examples, the housing can include more than one enlarged head. The implant may be configured for posterior lumbar interbody fusion (PLIF), or for anterior lumbar interbody fusion (ALIF).

In another exemplary embodiment, an expandable spinal implant can include a housing that includes an upper plate configured for placement against an endplate of a first vertebral body and a lower plate configured for placement against an endplate of a second, adjacent vertebral body. The expandable spinal implant may further include an integrated ratchet assembly within the housing that is configured to effect angular adjustment of the spinal implant. The ratchet assembly can include an elastically deformable plate connecting the upper and lower plates. The elastically deformable plate can have an edge configured to releasable engage a ratcheting pin, and a sleeve having a slotted opening for capturing the shaft. In use, the release of the pin from the sleeve allows the upper and lower plates to move apart and cause angular adjustment of the plates relative to one another.

In accordance to one aspect of the embodiment, the housing may include a porous surface. That porous surface may be on the upper or lower plate, or both. In some embodiments, a leading end of the implant is tapered. In addition, the housing may further include a bone graft window. The ratcheting pin may extend into an enlarged head for urging the upper and lower plates apart. The enlarged head may include a slot for engaging guide rails on the upper and lower plates. In addition, the upper and lower plates may further include steps for engaging the enlarged head. The implant may be configured for posterior lumbar interbody fusion (PLIF) or for anterior lumbar interbody fusion (ALIF).

Although the following discussion focuses on spinal implants, it will be appreciated that many of the principles may equally be applied to other structural body parts requiring bone repair or bone fusion within a human or animal body, including other joints such as knee, shoulder, ankle or finger joints.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 2A is a perspective view of an intervertebral cage constructed in accordance with another example, shown in an insertion configuration;

FIG. 2B is another perspective of the intervertebral cage illustrated in FIG. 2A;

FIG. 2C is a side view of the intervertebral cage illustrated in FIG. 2A;

DETAILED DESCRIPTION

Figure 1A:
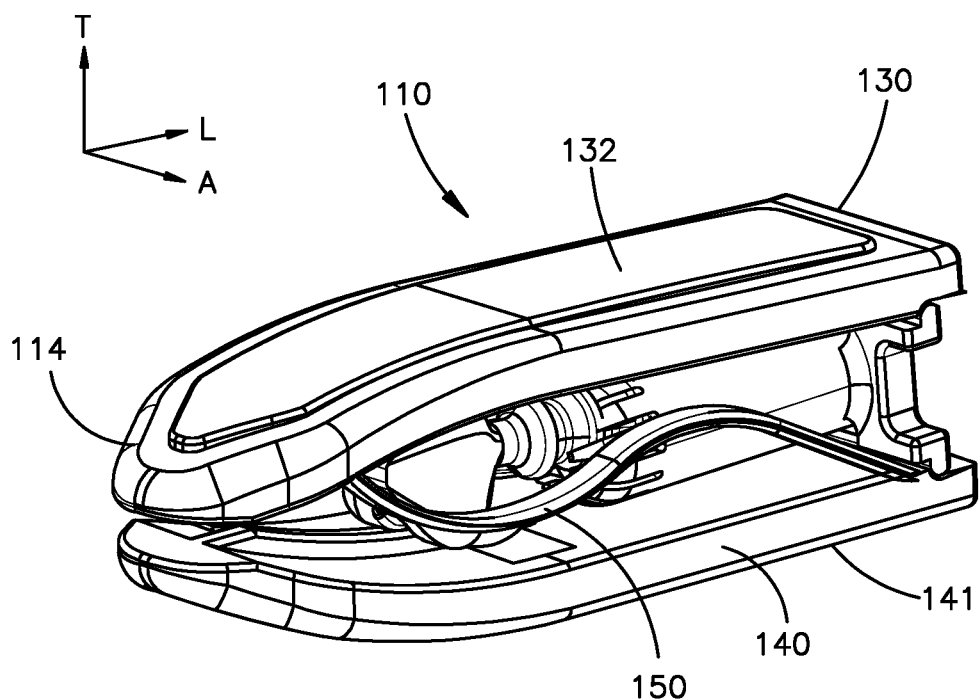
FIG. 1A is a perspective front view of an intervertebral cage constructed in accordance with one example, shown in an insertion configuration.

The present disclosure provides various spinal implant devices, such as interbody fusion spacers, or cages, for insertion between adjacent vertebrae. The devices can be configured for use in either the cervical or lumbar region of the spine. Thus, reference below to lordosis or lordotic angles can likewise apply to kyphosis or kyphotic angles. In some embodiments, these devices may be configured as ALIF cages, or LLIF cages.

These cages can restore and maintain intervertebral height of the spinal segment to be treated, and stabilize the spine by restoring sagittal balance and alignment. In some embodiments, the cages may have integrated ratchet assemblies that allow the cage to change size and angle as needed, with little effort. The cages may have a first or insertion configuration characterized by a first or reduced size to facilitate insertion through a narrow access passage and into the intervertebral space. The cages may be inserted in the first or insertion configuration, and then expanded to a second or expanded configuration having a second larger greater than the first or reduced size once implanted. In one example, the size can be defined by a height. In their second configuration, the cages are able to maintain the proper disc height and stabilize the spine by restoring sagittal balance and alignment. Additionally, the intervertebral cages are configured to be able to adjust the angle of lordosis, and can accommodate larger lordotic angles in their second, expanded configuration. Further, these cages may promote fusion to further enhance spine stability by immobilizing the adjacent vertebral bodies.

Additionally, the implantable devices may be manufactured using selective laser melting (SLM) techniques, a form of additive manufacturing. The devices may also be manufactured by other comparable techniques, such as for example, 3D printing, electron beam melting (EBM), layer deposition, and rapid manufacturing. With these production techniques, it is possible to create an all-in-one, multi-component device which may have interconnected and movable parts without further need for external fixation or attachment elements to keep the components together. Accordingly, the intervertebral cages of the present disclosure are formed of multiple, interconnected parts that do not require additional external fixation elements to keep together.

Further, devices manufactured in this manner can be constructed without connection seams, whereas devices traditionally manufactured include joined seams to connect one component to another. These connection seams can often represent weakened areas of the implantable device, particularly when the bonds of these seams wear or break over time with repeated use or under stress. By manufacturing the disclosed implantable devices using additive manufacturing, connection seams can be avoided entirely and therefore the problem is avoided.

In addition, by manufacturing these devices using an additive manufacturing process, all of the internal components of the device remain a complete construct during both the insertion process as well as the expansion process. That is, multiple components are provided together as a collective single unit so that the collective single unit is inserted into the patient, actuated to allow expansion, and then allowed to remain as a collective single unit in situ. In contrast to other cages requiring insertion of external screws or wedges for expansion, in the present embodiments the expansion and blocking components do not need to be inserted into the cage, nor removed from the cage, at any stage during the process. This is because these components are manufactured so as to be captured internally within the cages, and while freely movable within the cage, are already contained within the cage so that no additional insertion or removal is necessary.

In some embodiments, the cages can have an engineered cellular structure on a portion of, or over the entirety of, the cage. This cellular structure can include a network of pores, microstructures and nanostructures to facilitate osteosynthesis. For example, the engineered cellular structure can comprise an interconnected network of pores and other micro and nano sized structures that take on a mesh-like appearance. These engineered cellular structures can be provided by etching or blasting, to change the surface of the device on the nano level. One type of etching process may utilize, for example, HF acid treatment.

In addition, these cages can also include internal imaging markers that allow the user to properly align the cage and generally facilitate insertion through visualization during navigation. The imaging marker shows up as a solid body amongst the mesh under x-ray, fluoroscopy or CT scan, for example.

Another benefit provided by the implantable devices of the present disclosure is that they can be specifically customized to the patient's needs. Customization of the implantable devices is relevant to providing a preferred modulus matching between the implant device and the various qualities and types of bone being treated, such as for example, cortical versus cancellous, apophyseal versus central, and sclerotic versus osteopenic bone, each of which has its own different compression to structural failure data. Likewise, similar data can also be generated for various implant designs, such as for example, porous versus solid, trabecular versus non-trabecular, etc. Such data may be cadaveric, or computer finite element generated. Clinical correlation with, for example, DEXA data can also allow implantable devices to be designed specifically for use with sclerotic, normal, or osteopenic bone. Thus, the ability to provide customized implantable devices such as the ones provided herein allow the matching of the Elastic Modulus of Complex Structures (EMOCS), which enable implantable devices to be engineered to minimize mismatch, mitigate subsidence and optimize healing, thereby providing better clinical outcomes.

Figure 1B:
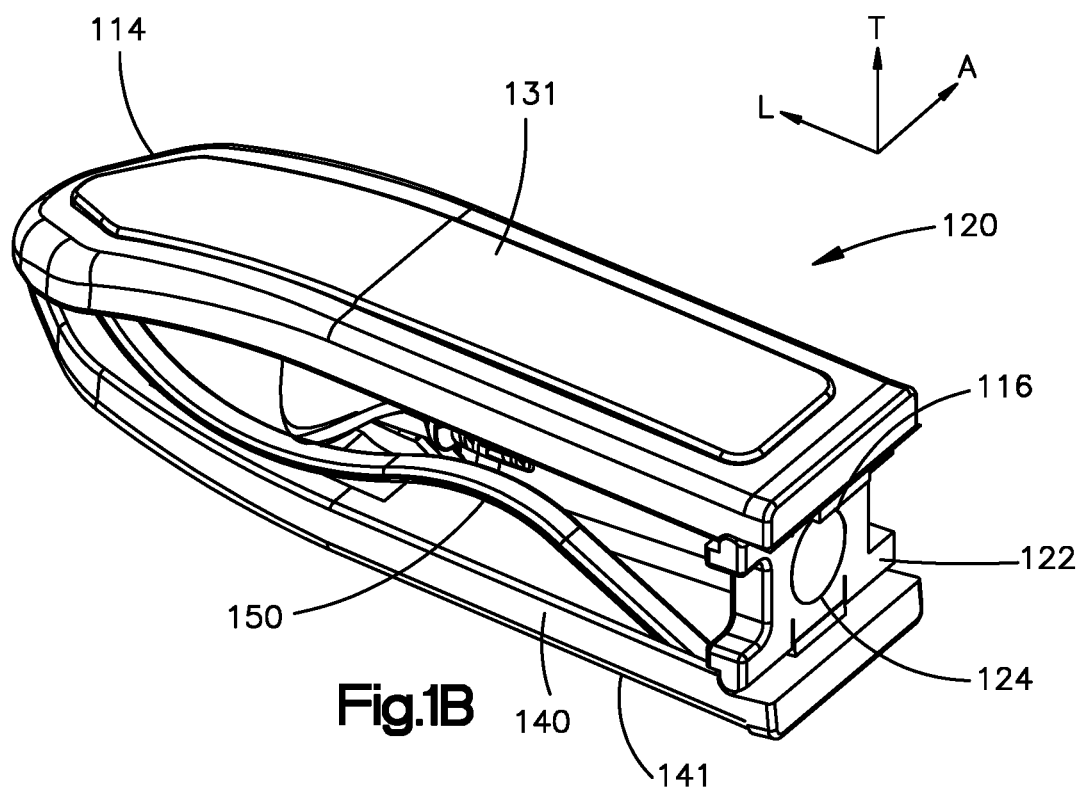
FIG. 1B is another perspective rear view of the intervertebral cage illustrated in FIG. 1A.

Turning now to the drawings, FIGS. 1A to 1E illustrate an example of an expandable and angularly adjustable intervertebral cage 110 of the present disclosure. FIGS. 1A and 1B show the intervertebral cage 110 in its smaller, insertion configuration. The intervertebral cage 110 can include a housing 120 that defines an upper plate 130 and a lower plate 140 that are configured to be placed against respective vertebral endplates of a pair of first and second adjacent vertebral bodies. In particular, the upper plate 130 can define an upper bearing surface 131 configured to abut the vertebral endplate of the first vertebral body. Similarly, the lower plate 140 can define a lower bearing surface 141 that is configured to abut the vertebral endplate of the second vertebral body. The first vertebral body can define a superior vertebral body, and the second vertebral body can define an inferior vertebral body. The upper and lower plates 130 and 140 can be opposite each other along a transverse direction T.

The intervertebral cage 110 has a front or leading end 114 with respect to the direction of insertion into the intervertebral disc space. The intervertebral cage 110 can further define a rear or trailing end 116 that is opposite the leading end 114 along a longitudinal direction L that is oriented perpendicular to the transverse direction T. The intervertebral cage 110 can define a length along the longitudinal direction L and a width along a lateral direction A that is perpendicular to each of the longitudinal direction L and the transverse direction T.

The intervertebral cage 110 can define a forward or leading direction that extends from the trailing end 116 toward the leading end 114. Thus, leading components of the intervertebral cage 110 can be spaced from trailing components of the intervertebral cage in the forward or leading direction. The intervertebral cage 110 can similarly define a rearward or trailing direction that extends from the leading end 114 toward the trailing end 116. In one embodiment, the leading end 114 can be tapered. For instance, one or both of the upper and lower plates 130 and 140 can taper toward the other as they extend in the forward direction at their respective front or leading ends. In one example, the intervertebral cage 110 can be configured for posterior lumbar interbody fusion (PLIF). Thus, once implanted, the leading end 114 can define an anatomically anterior end of the cage 110, and the trailing end 116 can define an anatomically posterior end of the cage 110. The width of the cage 110 can extend generally along the anatomical medial-lateral direction. As shown, the upper and lower plates 130 and 140 may have a porous structure 132 to facilitate cellular activity and bony ingrowth. The porous structure 132 can define the upper and lower bearing surfaces 131 and 141.

Figure 1C:
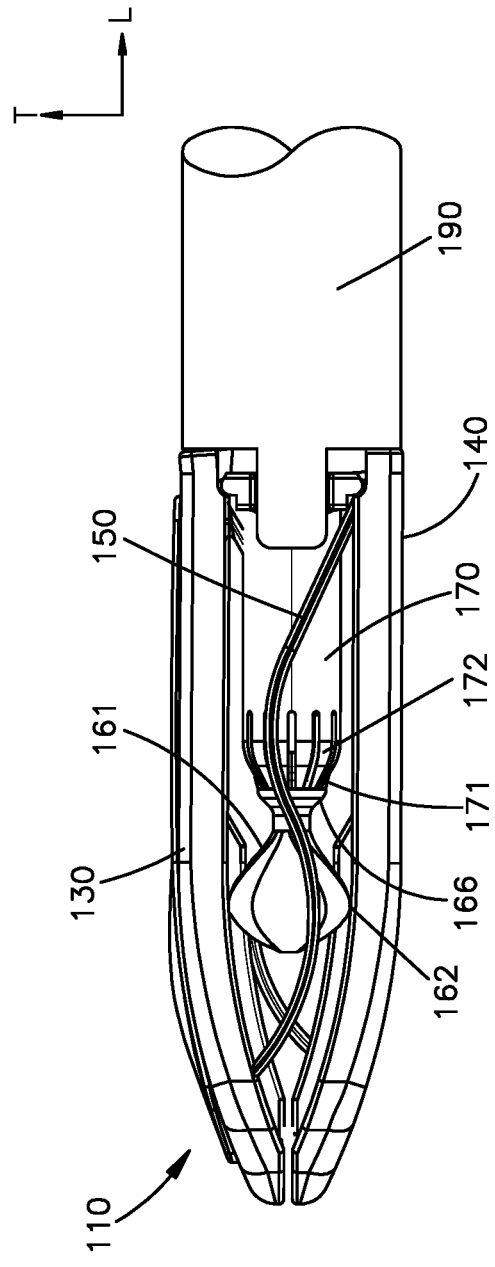
FIG. 1C is a side elevation view of the intervertebral cage illustrated in FIG. 1A.
Figure 1D:
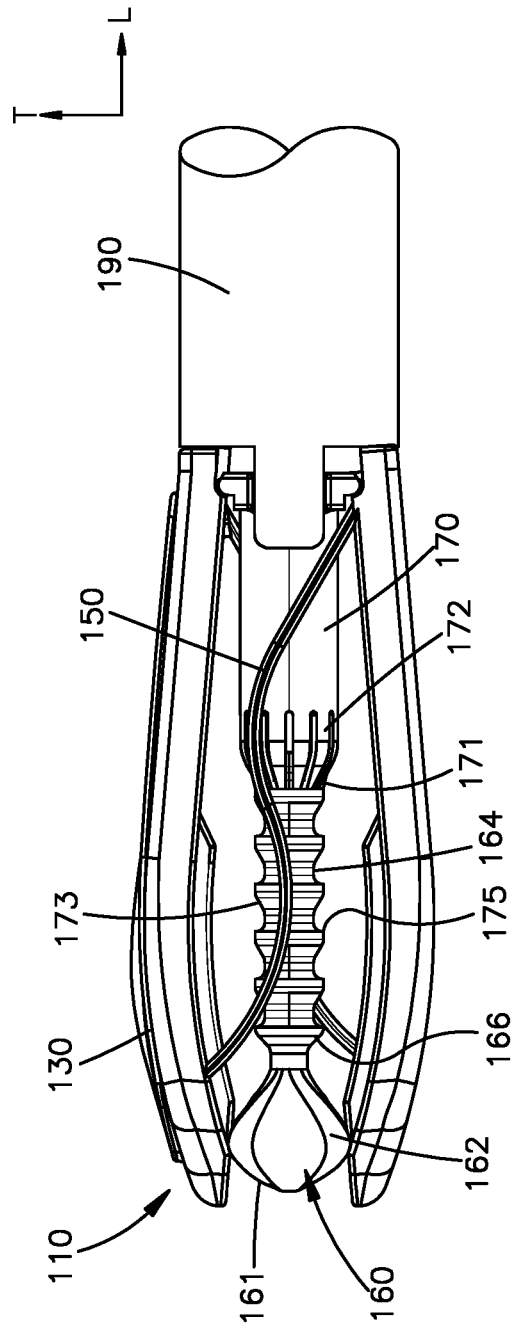
FIG. 1D is a side view of the intervertebral cage illustrated in FIG. 1A, shown in an expanded configuration.
Figure 1E:
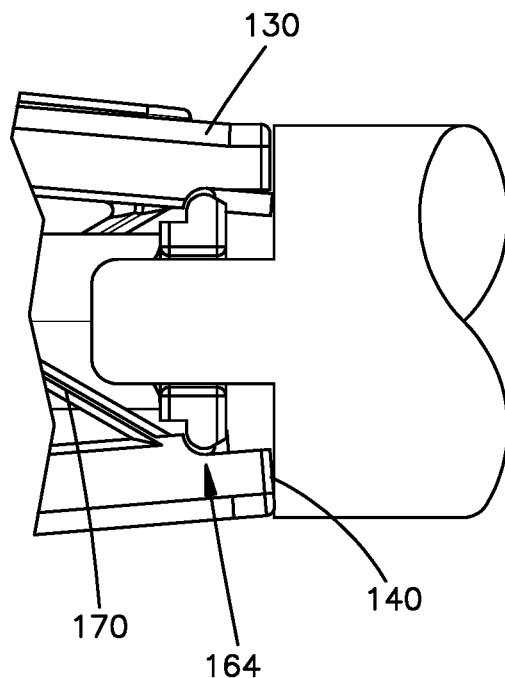
FIG. 1E is an exploded perspective view of a portion of the intervertebral cage illustrated in FIG. 1A showing the connection of upper and lower plates to a housing.

The intervertebral cage 110 can further include a hinge plate 122 that extends between the upper and lower plates 130 and 140 together. For instance, the hinge plate 122 can extend between the upper and lower plates 130 and 140 together at the rear of the housing 120. As shown in FIG. 1E, the upper and lower plates 130 and 140 can define a hinge with the hinge plate 122. For instance, one of the hinge plate 122 and the upper plate 130 can define a concave surface, and the other of the hinge plate 122 and the upper plate can define a convex surface. Similarly, one of the hinge plate 122 and the lower plate 140 can define a concave surface, and the other of the hinge plate 122 and the lower plate 140 can define a convex surface. In one example, the hinge plate 122 can define upper and lower convex surfaces, and the upper and lower plates 130 and 140 can define respective upper and lower concave surfaces that ride along the upper and lower convex surfaces of the hinge plate 122, respectively, as the intervertebral cage articulates. Alternatively, the hinge plate 122 can be monolithic with one of the upper plate 130 and the lower plate 140 so as to define a living hinge.

Figure 1F:
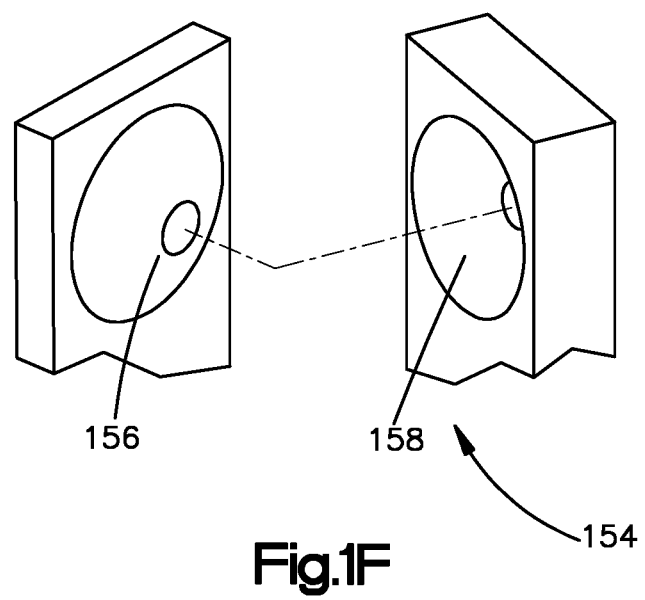
FIG. 1F is an exploded perspective view of a hinge constructed in accordance with an alternative embodiment.

Referring to FIG. 1F, in another example the intervertebral cage 110 can include a cone hinge 154 that hingedly attaches the upper and lower plates 130 and 140 to the housing 120. The cone hinge 154 can include a printed hinge that comprises a first plate that defines a projection 156 such as a cone or dome on one surface, and a second plate that defines a concavity, such as a cup 158 that extends into one surface. One or both of the first and second plates can be attached to the upper and lower plates 130 and 140, such that the intervertebral cage 110 articulates in the manner described herein.

With continuing reference to FIGS. 1A-1E generally, the intervertebral cage can further include at least one spring 150 that extends from the upper plate 130 to the lower plate 140. The spring 150 can apply a spring force against the upper and lower plates 140 that biases the upper and lower plates 130 and 140 toward the first or insertion configuration. Thus, the spring force can control movement of the upper and lower plates 130 and 140 relative to one another. It is appreciated that the upper and lower plates 130 and 140 are configured to overcome the spring force and move relative to one another in the manner described herein. In one example, the spring 150 can be configured as one or more elastically deformable strips 150 that are connected at their opposed free ends to the upper and lower plates 130 and 140, respectively.

The intervertebral cage 110 can further include an integrated ratchet assembly 160 that is fully integrated within the housing 120. In particular, the ratchet assembly 160 can be disposed between the upper and lower plates 130 and 140 with respect to the transverse direction T. The ratchet assembly 160 can include a ratchet shaft 164, and an engagement member 161 that is supported by the shaft 164 in the housing 120 at a location between the upper and lower plates 130 and 140 with respect to the transverse direction T. As will be described in more detail below, engagement member can be moved in the forward direction to urge the upper and lower plates 130 and 140 away from each other along the transverse direction. In particular, the ratchet assembly 160 operates by a pushing action, and in particular by pushing the engagement member 161 in the forward direction. The engagement member 161 can be configured as an enlarged head 162 having a greater cross-section than the shaft 164. In particular, the engagement member 161 can have a height that is greater than the distance between the upper and lower plates 130 and 140 along the transverse direction when the cage 110 is in its first or insertion configuration.

The shaft 164 can be elongated along the longitudinal direction L, and supports the engagement member 161 at a forward end of the shaft 164. The ratchet assembly 160 can further include a plurality of flanges 166 that extend out from the shaft 164 at a location rearward of the engagement member 161. The flanges 166 can be spaced from each other along the longitudinal direction L. As will be appreciated from the description below, the flanges 166 can define the ratchets of the ratchet assembly 160. The ratchet assembly 160 can further include a sleeve 170 that at least partially surrounds the shaft 164. When the ratchet assembly 160 is in a first or initial position, the flanges 166 can be disposed in the sleeve 170. Alternatively, one or more of the flanges 166 can be disposed forward of the sleeve 170. The sleeve 170 can have a flexible front opening 172 at a longitudinally front end of the sleeve 170.

In particular, the front end 171 of the sleeve 170 that defines the front opening 172 can be sized to receive the shaft 164, which can extend out of the sleeve in the forward direction through the front opening 172. The front end 171 of the sleeve 170 can be sized smaller than the outer cross-sectional dimension of the flanges 166 in a plane that is oriented perpendicular to the longitudinal direction L. The front end 171 of the sleeve 170 can be resiliently flexible, and configured to flex outward so as to allow the flanges 166 to move through the front opening 172 and out of the sleeve as the shaft 164 is moved forward along the longitudinal direction L. Thus, the flanges 166 ratchet through the front end 171 of the sleeve 170. In particular, the front end 171 of the sleeve 170 can flex around the flanges 166 as they are driven through the front opening 172. Thus, the flanges 166 can one-by-one (i.e., stepwise) be driven through the opening 172 at the front end 171 of the sleeve 170 in the forward direction. In one example, the front end 171 can be slotted and tapered inwardly as it extends in the forward direction. The shaft 164 defines a longitudinally rear end that is configured to engage an actuation instrument, which can also provide an insertion instrument. For instance, the longitudinally rear end of the sleeve 170 can be configured to receive the instrument.

As shown in FIG. 1B, the connection plate 122 can also include a longitudinal instrument-receiving opening 124. Thus, a dedicated instrument 190 can be inserted through the opening 124, and coupled to the integrated ratchet assembly 160 so as to deploy the ratchet assembly 160 within the housing 120. In particular, the instrument 190 can be inserted through the instrument-engaging opening 124 of the connection plate 122 until it engages the sleeve 170, as shown in FIGS. 1C and 1D. The instrument 190 can be configured to drive the shaft 164 in the forward direction. For instance, an inner pin of the instrument 190 can extend forward through an opening in the rear end of the sleeve 170, and apply a force against the shaft 164 that urges the shaft 164 to travel in the forward direction.

Referring to FIG. 1D, as the shaft 164 travels in the forward direction, the flanges 166 move through the front opening 172 and out the sleeve 170 in the manner described above. Each of the flanges 166 can define a first or front surface 173 and a second or rear surface 175 opposite the front surface 173 along the longitudinal direction L. The front surface 173 can be beveled to facilitate insertion of the flanges 166 through the front opening 172 of the sleeve 170.

In particular, the front surfaces 173 can flare rearwardly as they extend out from the shaft 164. The rear surfaces 175 can extend out from the shaft 164 along a direction substantially perpendicular to the central axis of the shaft 164. Thus, the rear surface 175 is configured to abut the front end 171 of the sleeve 170 when the shaft 164 is urged to move in the rearward direction. Abutment of the rear surface 175 against the front end of the sleeve 170 prevents the flanges 166 from being inserted into the sleeve 170 in the rearward direction. Thus, the rear surfaces 175 of the flanges 166 provide a stop surface that prevents movement of the shaft 164 in the rearward direction. Accordingly, the ratchet assembly 160 can be configured to permit forward movement of the shaft 164, but prevent rearward movement of the shaft 164. Alternatively, if desired, the flanges 166 can be configured to be driven through the opening 172 at the front end 171 of the sleeve in the rearward direction.

As the shaft 164 moves in the forward direction, which can be referred to as an expansion direction, the engagement member 161 moves with the shaft 164 in the forward direction. Thus, the engagement member 161 moves toward the front end 114 of the intervertebral cage 110. As the engagement member 161 moves in the forward direction at the front end 114 of the intervertebral cage 110, the engagement member 161 contacts respective transverse inner surfaces of each of the upper plate 130 and the lower plate 140. Because the transverse inner surfaces of at least one or both of the upper and lower plates 130 and 140 tapers toward the other along the transverse direction T in the manner described above, contact between the engagement member 161 and the upper and lower plates 130 and 140 urges the front ends of the upper and lower plates 130 and 140 to move away from each other along the transverse direction T. The engagement member 161 can have a sloped profile, and can be configured as a wedge as it forces the upper and lower plates 130 and 140 apart along the transverse direction T as it moves in the forward direction.

As described above, the upper and lower plates 130 and 140 can be hingedly fixed to each other at their respective rear ends. Thus, as the front ends of the upper and lower plates 130 and 140 move away from each other, the intervertebral cage 110 can assume a second or expanded configuration having a height at the front end that is greater than the height of the cage 110 in the first or insertion configuration. The height is measured along the transverse direction T. Further, the cage 110 can angulate as it expands from the first or insertion configuration to the second or expanded configuration. That is, the upper and lower plates 130 and 140 can define a first relative angular orientation when the cage 110 is in the first or initial configuration. The upper and lower plates 130 and 140 can define a second relative angular orientation when the cage 110 is in the second or expanded configuration. The second relative angular orientation can be different than the first relative angular orientation. The first and second relative angular orientations can be measured in a plane that is oriented along the longitudinal direction L and the transverse direction T. In one example, the upper and lower plates 130 and 140 can angulate about the hinge 154.

The cage 110 can be expanded along the transverse direction T and angulated in increments as the flanges 166 are driven out of the front end 171 of the sleeve 170. The closer the flanges 166 are spaced apart along the longitudinal direction L, the smaller the increments will be during expansion and angulation as the flanges 166 are individually driven out of the front end 171. Conversely, the further that the flanges 166 are spaced apart along the longitudinal direction L, the greater the increments will be during expansion and angulation as the flanges 166 are individually driven out of the front end 171. Thus, the cage 110 may be printed in one run, and provide small incremental adjustment of the height and angulation of the cage 110. The flanges 166 can be equidistantly spaced along the shaft 164 or variably spaced along the shaft 164. The shaft 164 can be prevented from translating rearwardly in response to compressive anatomical loads applied to the cage 110 along the transverse direction T during use.

As described above, the intervertebral cage 110 can be configured for posterior lumbar interbody fusion (PLIF), and the shaft 164 can be pushed in the forward direction by the instrument 190 so as to actuate the intervertebral cage 110 from the first or insertion configuration to the second or expanded configuration. It is understood, however, that the intervertebral cage 110 can be configured for anterior lumbar interbody fusion (ALIF). As described in more detail below, when the intervertebral cage 110 is configured as an ALIF cage, the ratchet assembly 160 can be actuated by pulling the shaft 164 in the forward direction.

The intervertebral cage 110 can have any suitable dimension as desired. In one example where the cage 110 is configured as a PLIF cage, the dimensions can be any one of 22×9, 26×9, 30×9, 34×9, 22×11, 26×11, and 30×11 (Length×Width), with the stated dimensions in mm. Thus, the length of the cage 110 along the longitudinal direction L can be in a range from approximately 22 mm to approximately 34 mm, including any one of approximately 22 mm, approximately 26 mm, approximately 30 mm, and approximately 34 mm. The term "approximate" recognizes manufacturing tolerances and other potential variations, and includes plus or minus 10% of the stated number. The width of the cage 110 along the lateral direction A can be in a range from approximately 9 mm to approximately 11 mm. The height of the cage 110 from the upper bearing surface 131 to the lower bearing surface 141 along the transverse direction can range from approximately 7 mm to approximately 16 mm, in 1 mm increments, when the cage 110 is in the first or insertion configuration. Further, as the cage expands from the first configuration to the second configuration, the cage 110 can angulate in a range from approximately zero degrees to approximately 18 degrees, including approximately 4 degrees, approximately 6 degrees, and approximately 12 degrees. As described above, the leading end 114 can be expanded along the transverse direction relative to the trailing end 116 as the cage 110 expands and angulates. It should be appreciated that the above values are presented as examples only, and that the cage 210 can alternatively be configured as desired.

Figure 2D:
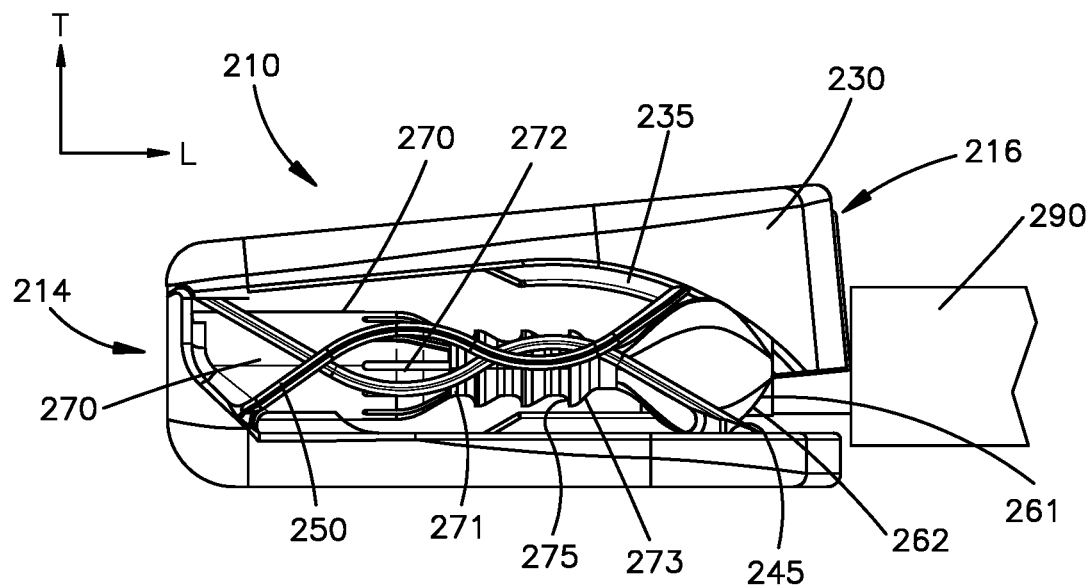
FIG. 2D is a side view of the intervertebral cage illustrated in FIG. 2A, shown in an expanded configuration.
Figure 2E:
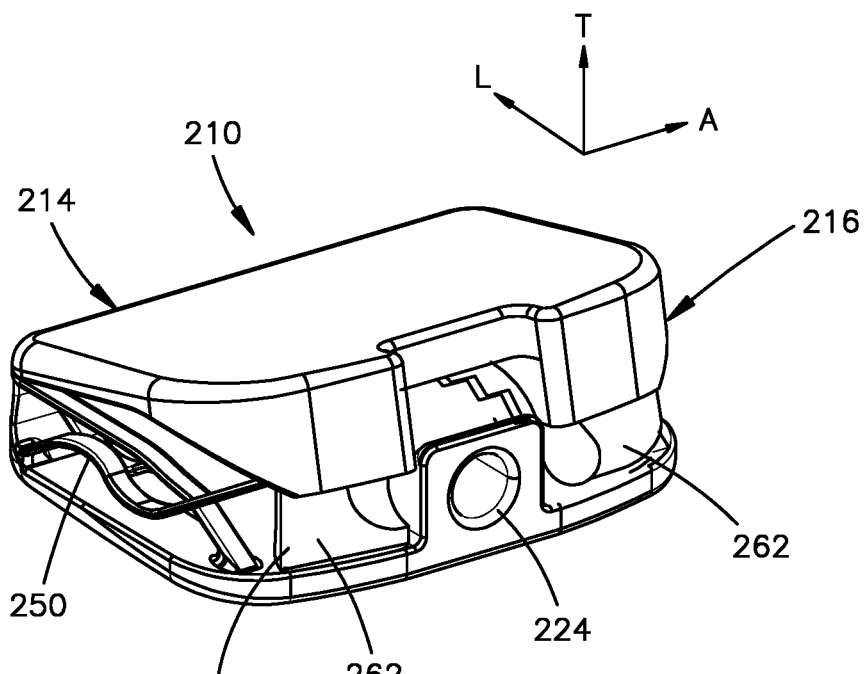
FIG. 2E is a perspective view of the intervertebral cage illustrated in FIG. 2D.

FIGS. 2A to 2F illustrate another example of an intervertebral cage 210. The cage 210 shares similar features described above with respect to the cage 110, but is configured for an anterior lumbar interbody fusion (ALIF). FIGS. 2A and 2B show the intervertebral cage 210 in its smaller, insertion configuration. As described above with respect to the cage 110, the intervertebral cage 210 can include a housing 220 that that defines an upper plate 230 and a lower plate 240 that are configured to be placed against the respective vertebral endplates. In particular, the upper plate 230 can define an upper bearing surface 231 configured to abut the vertebral endplate of the first vertebral body. Similarly, the lower plate 140 can define a lower bearing surface 241 that is configured to abut the vertebral endplate of the second vertebral body. The upper and lower plates 230 and 240 can be opposite each other along a transverse direction T.

The intervertebral cage 210 has a front or leading end 214 with respect to the direction of insertion into the intervertebral disc space. The intervertebral cage 210 can further define a rear or trailing end 216 that is opposite the leading end 214 along a longitudinal direction L that is oriented perpendicular to the transverse direction T. The intervertebral cage 210 can define a length along the longitudinal direction L and a width along a lateral direction A that is perpendicular to each of the longitudinal direction L and the transverse direction T.

The intervertebral cage 210 can define a forward or leading direction that extends from the trailing end 216 toward the leading end 214. Thus, leading components of the intervertebral cage 210 can be spaced from trailing components of the intervertebral cage in the forward or leading direction. The intervertebral cage 210 can similarly define a rearward or trailing direction that extends from the leading end 214 toward the trailing end 216. In one embodiment, the leading end 214 can be tapered. In one example, the intervertebral cage 210 can be configured for posterior lumbar interbody fusion (ALIF). Thus, once implanted, the leading end 214 can define an anatomically posterior end of the cage 210, and the trailing end 216 can define an anatomically anterior end of the cage 210. The width of the cage 210 can extend generally along the anatomical medial-lateral direction. As shown, the upper and lower plates 230 and 240 may have a porous structure 232 to facilitate cellular activity and bony ingrowth. The porous structure 232 can define the upper and lower bearing surfaces 231 and 241.

The intervertebral cage 210 can further include a rear plate 222 that extends from one of the upper plate 230 and the lower plate 240. In one example, the rear plate 222 can extend up from the lower plate 240 at the trailing end 216 of the cage 210. Further, the leading end of the cage 210 can include a hinge plate that extends between the upper plate 230 and the lower plate 240 at the leading end 214 of the cage 210. The hinge plate can be constructed as described above with respect to the hinge plate 122. Alternatively, the hinge plate can be monolithic with one or both of the upper and lower plates 230 and 240 so as to define one or more living hinges. For instance, the connection plate 222 can connect the upper and lower plates 230 and 240 together at the front of the housing 220. In addition, referring also to FIG. 2C, the intervertebral cage 210 can further include at least one spring 250 that extends from the upper plate 230 to the lower plate 240. The spring 250 can apply a spring force against the upper and lower plates 230 and 240 that biases the upper and lower plates 230 and 240 toward the first or insertion configuration. Thus, the spring force can control movement of the upper and lower plates 230 and 240 relative to one another. It is appreciated that the upper and lower plates 230 and 240 are configured to overcome the spring force and move relative to one another in the manner described herein. In one example, the spring 250 can be configured as one or more elastically deformable strips 250 that are connected at their opposed free ends to the upper and lower plates 230 and 240, respectively. In one example, each lateral side of the cage 210 can include a pair of deformable strips that are positioned adjacent each other and are mirror images of each other.

Figure 2F:
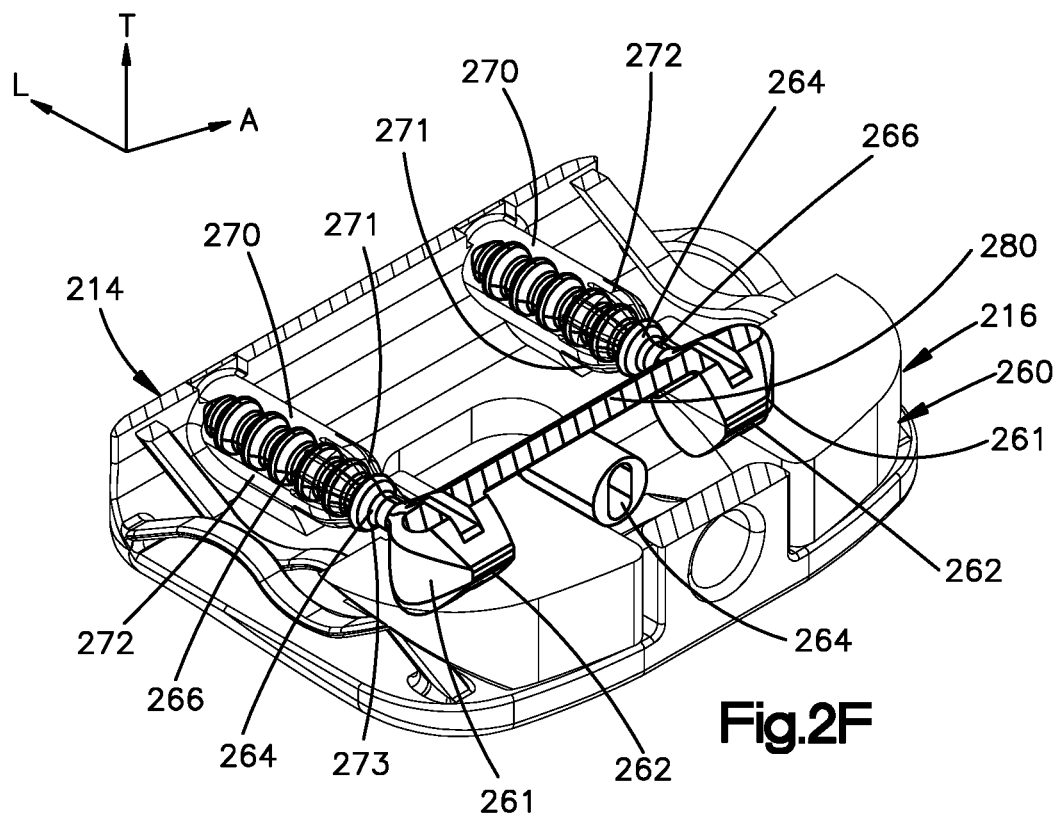
FIG. 2F is a perspective view of the intervertebral cage illustrated in FIG. 2E, with portions cut away.

Referring now also to FIG. 2F, the intervertebral cage 110 can further include an integrated ratchet assembly 260 that is fully integrated within the housing 220. In particular, the ratchet assembly 260 can be disposed between the upper and lower plates 230 and 240 with respect to the transverse direction T. The ratchet assembly 160 can include at least one ratchet shaft 264 and at least one engagement member 261 that is supported by the shaft 264 in the housing 220 at a location between the upper and lower plates 230 and 240 with respect to the transverse direction T. For instance, the ratchet assembly 260 can include first and second engagement shafts 264 and first and second members 261 that are supported by respective ones of the shafts 264. The engagement members 261 can be spaced from each other along the lateral direction A. The first and second engagement members 261 can be equidistantly spaced from the longitudinal central axis of the cage 210, or can be otherwise positioned as desired. It should be appreciated that the ratchet assembly 160 described above can similarly include first and second engagement members 161 as described herein with respect to the ratchet assembly 260. Alternatively, the ratchet assembly 260 can include a single engagement member 261 as described above with respect to the ratchet assembly 160.

As will be described in more detail below, the engagement members 261 can be moved in the rearward direction to urge the upper and lower plates 230 and 240 away from each other along the transverse direction T. In particular, the ratchet assembly 260 can operates by a pulling action, and in particular by pulling the engagement members 261 in the rearward direction toward the trailing end 216. The engagement members 161 can be configured as enlarged heads 162 having a greater cross-section than the shaft 264. In particular, the engagement members 261 can have a height that is greater than the distance between the upper and lower plates 230 and 240 along the transverse direction T when the cage 210 is in its first or insertion configuration.

The shafts 264 can be elongate along the longitudinal direction L, and can support the engagement members 261 at respective rear ends of the shaft 264. The ratchet assembly 260 can further include a plurality of flanges 266 that extend out from each of the shafts 264 at a location forward of the engagement member 261. The flanges 266 can be spaced from each other along the longitudinal direction L. As will be appreciated from the description below, the flanges 266 can define the ratchets of the ratchet assembly 260. The ratchet assembly 260 can further include first and second sleeves 170 that at least partially surrounds respective ones of the shafts 264. When the ratchet assembly 260 is in a first or initial position, the flanges 266 can be disposed in the sleeves 270. Alternatively, one or more of the flanges 266 can be disposed rearward of the sleeve 270. The sleeves 270 can have a flexible front opening 272 at a longitudinally rear end 271 of the sleeves 270. The rear end 271 of the sleeves 270 can be constructed as described above with respect to the front end 171 of the sleeve 170.

As shown in FIGS. 2B-2C, the rear plate 222 can also include a longitudinal instrument-receiving opening 224. Thus, a dedicated instrument 290 can be inserted through the opening 224, and coupled to the integrated ratchet assembly 260 so as to deploy the ratchet assembly 260 within the housing 220. In particular, the instrument 290 can be inserted through the instrument-engaging opening 224 of the rear plate 222 until it engages the sleeve 270. The ratchet assembly 260 can further include a pull bar 280 that extends from the first shaft 264 or supported actuation member 261 to the second shaft 164 or supported actuation member 261 generally along the lateral direction A. The instrument 290 can be configured to engage the pull bar 280 so as to drive each of the shafts 264 and supported engagement members 261 in the rearward direction in a pulling motion.

Referring to FIG. 1D, as the shafts 264 travel in the rearward direction, the flanges 266 move through the front openings 272 of the respective sleeve 270 and out the respective sleeve 270 in the manner described above. Each of the flanges 266 can define a first or rear surface 273 and a second or front surface 275 opposite the rear surface 273 along the longitudinal direction L. The rear surface 273 can be beveled to facilitate insertion of the flanges 266 through the front openings 272 of the sleeves 270. In particular, the rear surfaces 273 can flare forwardly as they extend out from the shaft 264. The front surfaces 275 can extend out from the shaft 264 along a direction substantially perpendicular to the central axis of the shaft 264. Thus, the front surfaces 275 are configured to abut the rear ends 271 of the respective sleeves 270 when the shaft 264 is urged to move in the rearward direction. Abutment of the front surface 275 against the front end of the sleeve 270 prevents the flanges 266 from being inserted into the sleeve 270 in the forward direction. Thus, the front surfaces 275 of the flanges 266 provide a stop surface that prevents movement of the shaft 164 in the forward direction that would collapse the cage 210 once expanded. Accordingly, the ratchet assembly 260 can be configured to permit rearward movement of the shaft 264, but prevent forward movement of the shaft 264. Alternatively, if desired, the flanges 266 can be configured to be driven through the opening 272 at the front end 271 of the respective sleeve 270 in the forward direction.

As the shafts 264 move in the rearward direction, which can be referred to as an expansion direction, the engagement members 261 moves with the shaft 264 in the rearward direction. Thus, the engagement members 261 moves toward the rear end 214 of the intervertebral cage 210. As the engagement members 261 move in the rearward direction at the rear end 141 of the intervertebral cage 110, the engagement members 161 contact respective transverse inner surfaces 235 and 245, respectively, of each of the upper plate 230 and the lower plate 240. One or both of the transverse inner surfaces 235 and 245 can taper toward the other of the transverse inner surfaces 235 and 245 along the transverse direction T as they extend in the rearward direction. In one example, the upper transverse surface 235 can taper more than the lower transverse surface 245. It should be appreciated, of course, that the transverse inner surfaces 235 and 245 can alternatively taper equally, or one can taper while the other does not.

It should thus be appreciated that the distance between the transverse inner surfaces 235 and 245 along the transverse direction T decreases as the transverse inner surfaces 235 and 245 extend in the rearward direction. Accordingly, contact between the engagement members 161 and the transverse inner surfaces 235 and 245 urges the rear ends of at least one or both of the upper and lower plates 230 and 240 to move away from the other of the upper and lower plates 230 and 240 along the transverse direction T, thereby expanding the cage 210. The engagement members 261 can each have a sloped profile, and can be configured as a wedge as it forces one or both of the upper and lower plates 230 and 240 apart along the transverse direction T as it moves in the rearward direction.

As described above, the upper and lower plates 230 and 240 can be hingedly fixed to each other at their respective rear ends. Thus, as the rear ends of the upper and lower plates 230 and 240 move away from each other, the intervertebral cage 210 can assume a second or expanded configuration having a height that is greater than the height of the cage 210 in the first or insertion configuration. The height is measured along the transverse direction T. Further, the cage 210 can angulate as it expands from the first or insertion configuration to the second or expanded configuration. That is, the upper and lower plates 230 and 240 can define a first relative angular orientation when the cage 210 is in the first or initial configuration. The upper and lower plates 230 and 240 can define a second relative angular orientation when the cage 210 is in the second or expanded configuration. The second relative angular orientation can be different than the first relative angular orientation. The first and second relative angular orientations can be measured in a plane that is oriented along the longitudinal direction L and the transverse direction T. In one example, the upper and lower plates 230 and 240 can angulate about the hinge 254.

The cage 210 can be expanded along the transverse direction T and angulated in increments as the flanges 266 are driven out of the opening 272 at the rear end 271 of the sleeve 270. The closer the flanges 266 are spaced apart along the longitudinal direction L, the smaller the increments will be during expansion and angulation as the flanges 266 are individually driven out of the front end 271. Conversely, the further that the flanges 266 are spaced apart along the longitudinal direction L, the greater the increments will be during expansion and angulation as the flanges 266 are individually driven out of the front end 271. Thus, the cage 210 may be printed in one run, and provide small incremental adjustment of the height and angulation of the cage 210. The flanges 166 can be equidistantly spaced along the respective shafts 164 or variably spaced along the respective shafts 164. The shafts 264 can be prevented from translating along a forward direction, also referred to as a contraction direction, in response to compressive anatomical loads applied to the cage 210 along the transverse direction T during use.

As described above, the intervertebral cage 110 can be configured for anterior lumbar interbody fusion (ALIF), and the shafts 264 can be driven in the rearward direction by the instrument 290 so as to actuate the intervertebral cage 210 from the first or insertion configuration to the second or expanded configuration. It is understood, however, that the intervertebral cage 210 can be configured for posterior lumbar interbody fusion (PLIF), in which case the ratchet assembly 160 can be actuated by driving the shafts 264 in the forward direction as described above with respect to the cage 110.

The intervertebral cage 210 can have any suitable dimension as desired. In one example where the cage 210 is configured as a ALIF cage, the dimensions can be any one of 34×25 37×27, 40×29, 45×32 (Length×Width), with the stated dimensions in mm. Thus, the length of the cage 210 along the longitudinal direction L can be in a range from approximately 34 mm to approximately 45 mm, including any one of approximately 34 mm, approximately 37 mm, approximately 40 mm, and approximately 45 mm. The term "approximate" recognizes manufacturing tolerances and other potential variations, and includes plus or minus 10% of the stated number. The width of the cage 210 along the lateral direction A can be in a range from approximately 25 mm to approximately 32 mm. The height of the cage 210 from the upper bearing surface 231 to the lower bearing surface 241 along the transverse direction can range from approximately 8 mm to approximately 20 mm, in 1 mm increments, when the cage 210 is in the first or insertion configuration. Further, as the cage expands from the first configuration to the second configuration, the cage 210 can angulate in a range from approximately zero degrees to approximately 20 degrees, including approximately 5 degrees, approximately 10 degrees, approximately 15 degrees, and approximately 20 degrees. As described above, the trailing end 216 can be expanded along the transverse direction relative to the leading end 214 as the cage 210 expands and angulates. It should be appreciated that the above values are presented as examples only, and that the cage 210 can alternatively be configured as desired.

Figure 3:
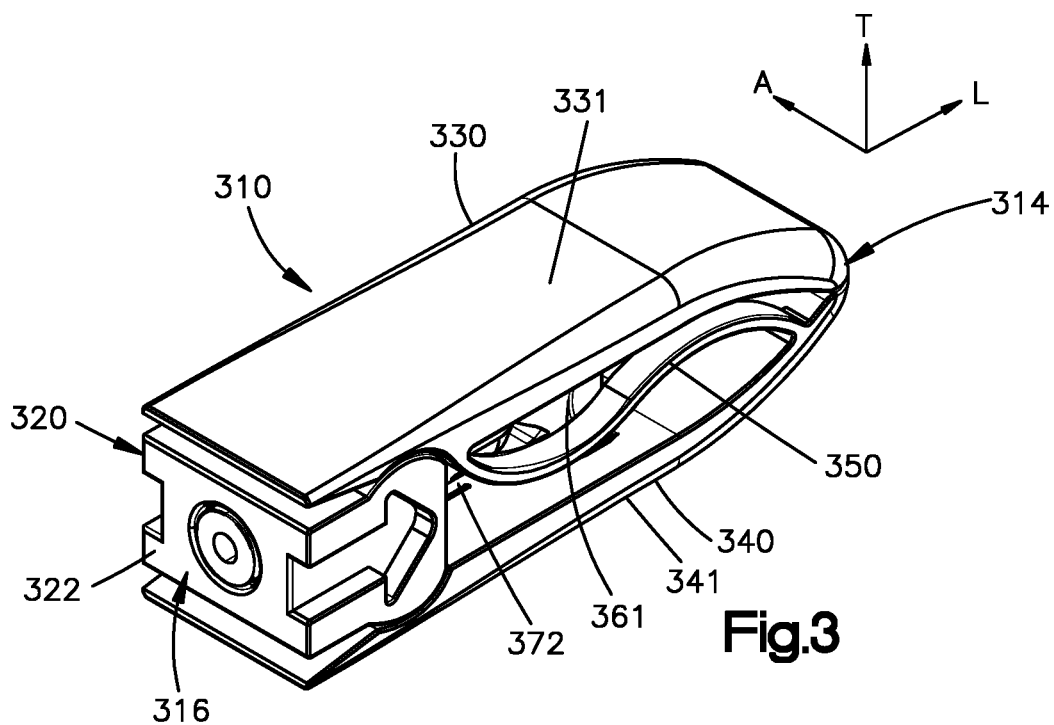
FIG. 3 is a perspective rear view of an intervertebral cage constructed in accordance with another example.

FIG. 3 illustrates yet another exemplary embodiment of an intervertebral cage 310 of the present disclosure. The intervertebral cage 310 can be constructed as described above with respect to each of the cages 110 and 210. In FIG. 3, reference numerals corresponding to like elements of those described above have been incremented by 100 or 200 for the purposes of clarity and convenience. The cage 310 can have a housing 320 that includes upper and lower plates 330, 340 that are connected to the housing 320 by a plate 322, and has an integrated ratchet assembly configured to expand the cage 310. The integrated ratchet assembly can be constructed as described above with respect to either of the ratchet assembly 160 or the ratchet assembly 260. Further, the cage 310 can be an ALIF cage, a PLIF cage, or any suitable alternatively configured cage. In some examples, such as the one shown, one or both of the upper and lower plates 330 and 340 do not contain the porous structure described herein. Thus, the corresponding one or both of the upper and lower bearing surfaces 331 and 341 of the upper and lower plates 330 and 340, respectively, are not defined by a porous structure in some examples. Instead, the corresponding one or both of the upper and lower bearing surfaces 331 and 341 can be substantially smooth and continuous from the leading end to the trailing end of the cage along the longitudinal direction L, and from a first lateral side to a second lateral side of the cage 310 along the lateral direction A.

Figure 4A:
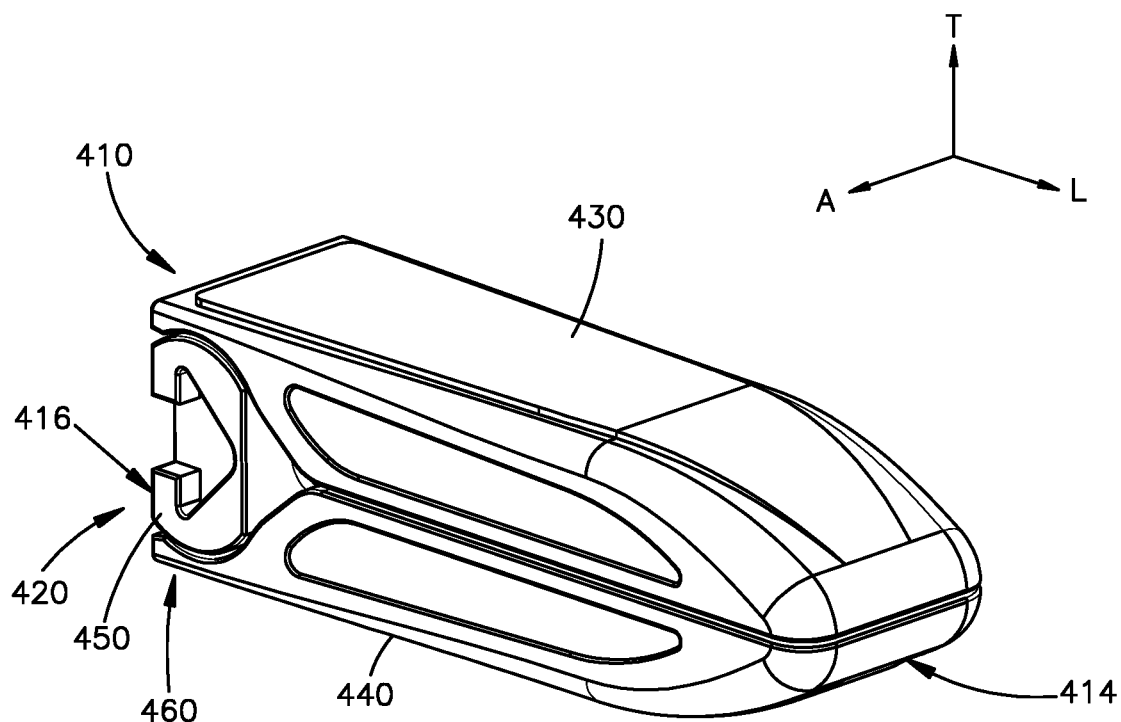
FIG. 4A is a perspective view of an intervertebral cage constructed in accordance with another embodiment, shown in an unexpanded, insertion configuration.
Figure 4B:
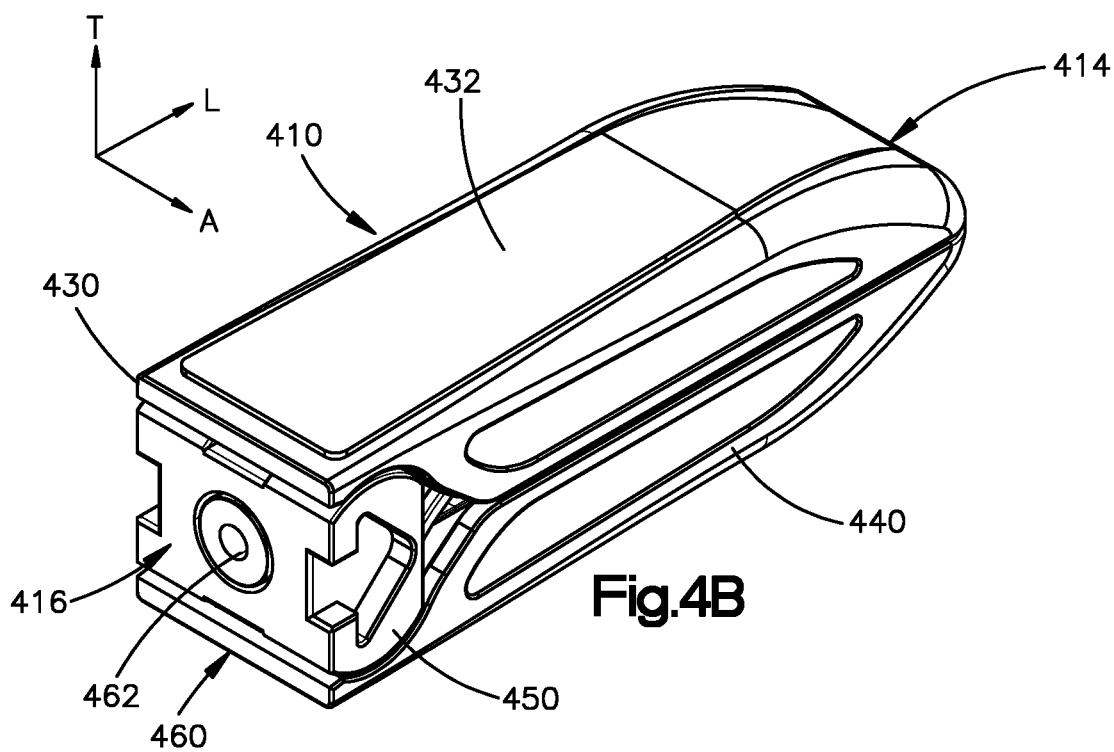
FIG. 4B is another perspective view of the intervertebral cage illustrated in FIG. 4A.
Figure 4C:
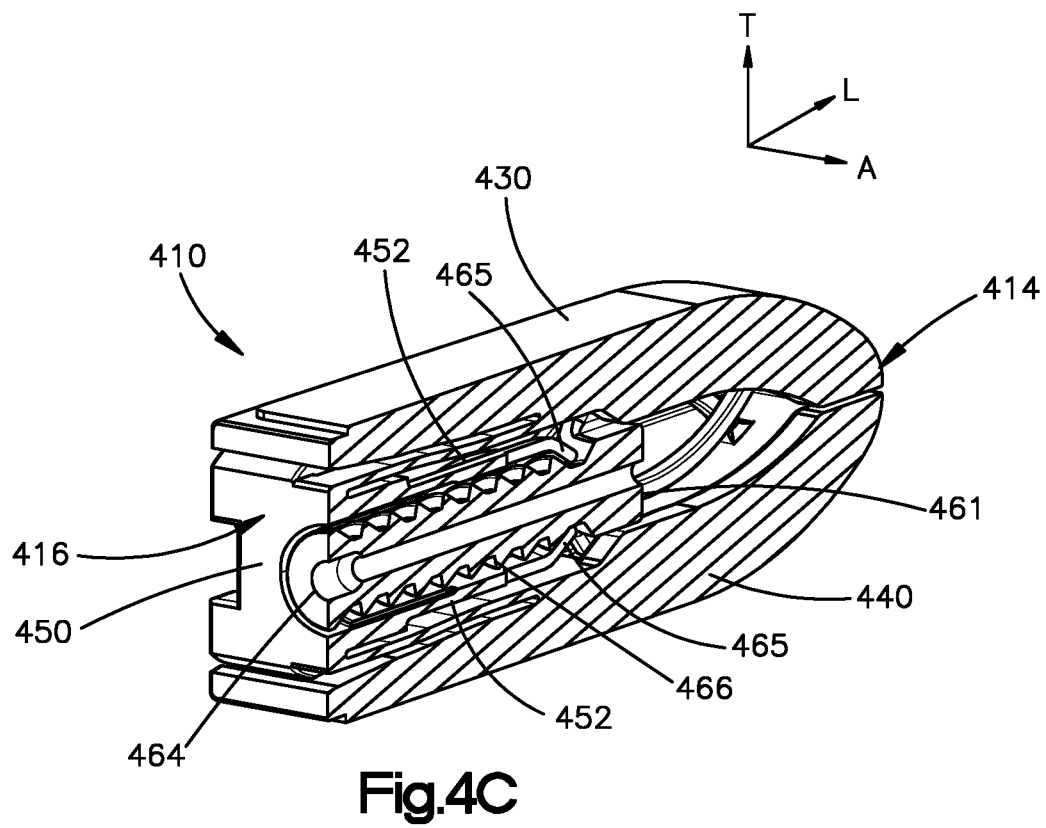
FIG. 4C is a cross-sectional perspective view of the intervertebral cage illustrated in FIG. 4A.
Figure 4D:
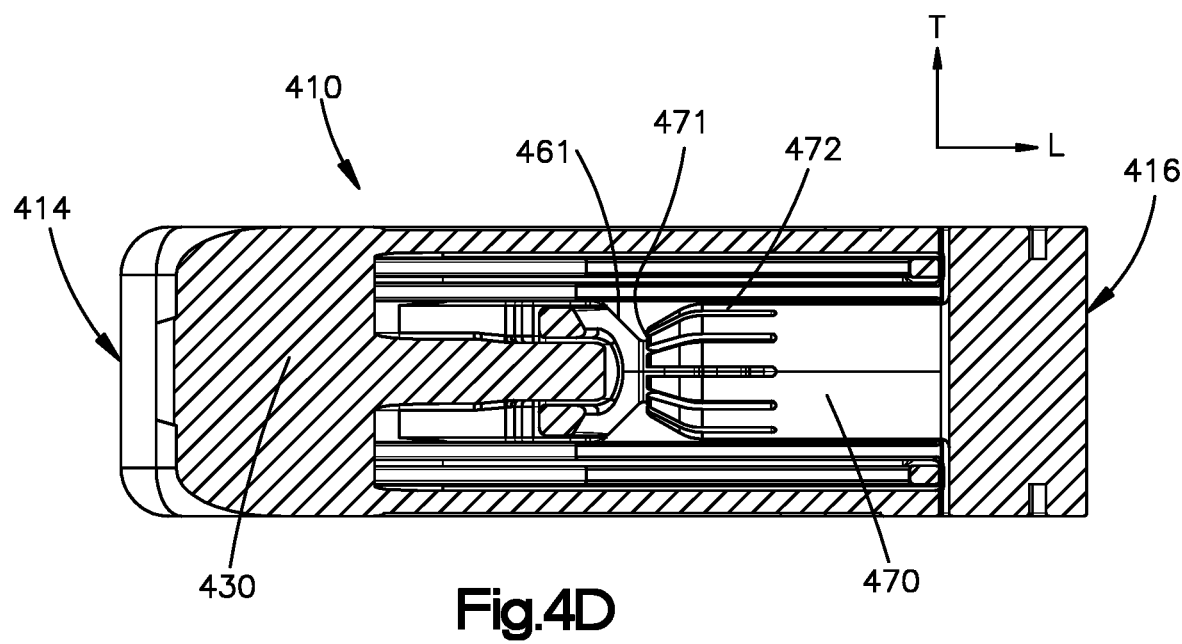
FIG. 4D is a sectional top view of the intervertebral cage illustrated in FIG. 4A.

FIGS. 4A to 4D illustrate still another example of an intervertebral cage 410 of the present disclosure. FIGS. 4A and 4B show the intervertebral cage 410 in its smaller, insertion configuration. In FIGS. 4A-4D, reference numerals corresponding to like elements of those described above have been incremented by 100, 200, or 300 for the purposes of clarity and convenience. The intervertebral cage 410 may comprise a housing 420 defined by a pair of plates 430 and 440 configured for placement against endplates of a pair of adjacent vertebral bodies. As shown, the plates 430 and 440 may have a porous structure 432 to facilitate cellular activity and bony ingrowth in the manner described above.

The plates 430 and 440 are connected together at the rear end 416 of the housing 420 by an elastic interconnection 450. The elastic interconnection 450 can be defined by an elastic interconnected plate 452 that is disposed between the plates 430 and 440. In particular, the elastic interconnected plate 452 can define one or more longitudinally extending arms that can be configured to resiliently flex as the cage 410 expands. Thus, the arms can define a biasing force that urges the cage 410 toward its first configuration. The arms of the interconnected plate 452 can define an opening that receives a ratchet shaft 464. The upper and lower plates 430 and 440 and the interconnected plate 452 can define a single monolithic structure. The ratchet shaft 464 can be driven in the expansion direction, which causes the ratchet shaft 464 to ride along inner ramps of the upper and lower plates 430 and 440, thereby expanding the cage 410. In one example, the ratchet shaft 464 can push the respective front ends of the upper and lower plates 430 and 440 away from each other as it rides over the inner ramps, thereby causing the cage 410 to angulate. In particular, the leading end 414 of the cage 410 expands along the transverse direction T relative to the trailing end 416. Thus, engagement between each of the upper and lower plates 430 and 440 and the ratchet shaft 464 prevents the flexible arms of the interconnected plate 452 from driving the cage 410 to the first configuration. The cage 410 can be a PLIF cage, and thus the expansion direction can be defined by the forward direction. It should be appreciated, of course, that the cage 410 can alternatively be configured as an ALIF cage, in which case the expansion direction would be defined by the rearward direction. The flanges 466 that extend out from the shaft 464 can cooperate with the tapered open end 472 of the sleeve 470 in the manner described above. The opposed rear end of the sleeve 270 can be secured within the housing 420.

The elastic interconnected plate 452 can define at least one an inwardly projecting tooth 465, such as an upper and lower tooth 465 that engages with the flanges 466 of the ratchet assembly. Accordingly, as the shaft 464 is incrementally driven out of the open end 472 of the sleeve 470 in the expansion direction, the elastic interconnected plate 452 is likewise incrementally driven in the expansion direction, which is the forward direction as illustrated, which thereby allows the interconnected plates 430 and 440 to expand in increments along the transverse direction T as described above. As the cage 410 expands from the first configuration to the second configuration, the cage 410 can angulate in a range from approximately zero degrees to approximately 18 degrees, including approximately 4 degrees, approximately 8 degrees, approximately 12 degrees, and approximately 16 degrees, as one example.

Figure 5:
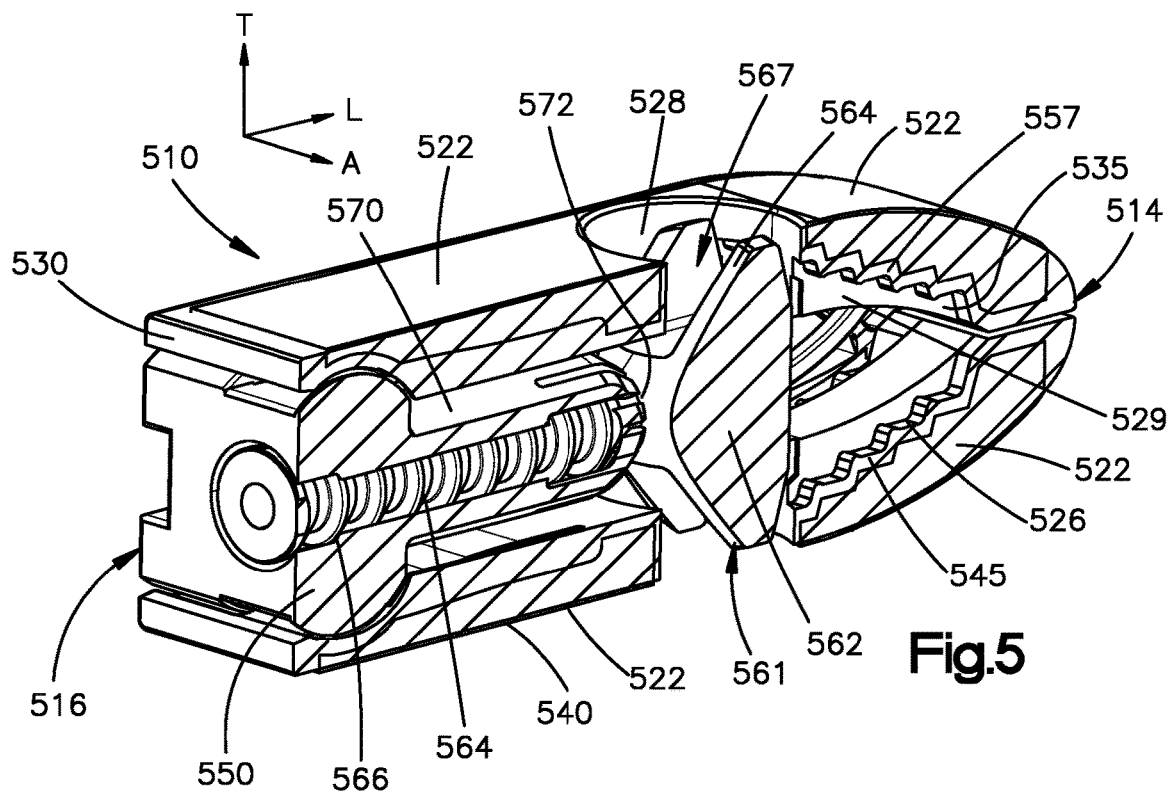
FIG. 5 is a cross-sectional perspective view of an intervertebral cage constructed in accordance with another example, shown in an unexpanded, insertion configuration.

FIG. 5 illustrates yet still another example of an intervertebral cage of the present disclosure. In FIG. 5, reference numerals corresponding to like elements of those described above have been incremented by 100, 200, 300, or 400 for the purposes of clarity and convenience. As shown, the intervertebral cage 510 shares similar features to intervertebral cage 410, but now also has more engineered porous structures 522 to maximize the porous nature of the cage 510. In some example, the porous structure 522 can have a thickness that ranges from approximately 0.5 mm to approximately 1 mm, though it should be appreciated that the porous structure can have any suitable thickness as desired. Further, in some example, the thickness of the porous structure 522 can range from approximately 1/10 and approximately 2/3 the height of the plate thickness along the transverse direction T. As described herein with respect to the other cages, the cage 510 includes a housing 520 having an upper plate 530 and lower plate 540, and an elastic interconnection that connects the upper and lower plates 530 and 540 together at the rear end 516 of the housing 520. The cage 510 can further include a bone graft window 528 that extends through one or both of the upper plate 530 and the lower plate 450. The window 528 of the upper plate 530 can be aligned with the window 528 of the lower plate 540 along the transverse direction T.

As described above with respect to the other cages, the cage 510 can include a plurality of flanges 566 that extend out from the ratchet shaft 564. The engagement member 561, which can be configured as an enlarged head 562, extends out from the shaft 564 at a location spaced from the flanges 566 in the expansion direction. One or both of the upper and lower plates 530 and 540 can include a guide rail 529 that extends along the longitudinal direction L. The guide rail 529 can extend from the transverse inner surface 535 and 545 of one or both of the upper and lower plates 530 and 540. The engagement member 561 can include a guide slot 567 that extends through the engagement member 561 along the longitudinal direction L, and is sized to receive the guide rail 529, such that the engagement member 561 travels along the guide rail 529 as the shaft 564 is driven in the expansion direction. It should be appreciated that any of the ratchet assemblies described herein can include a guide rail that is received in a guide slot of the respective engagement member.

Further, the inner transverse surface 535 and 545 of one or both of the upper and lower plates 530 and 540, respectively, can define a plurality of steps 557. The steps 557 can be arranged so as to extend transversely inward as they extend along the expansion direction. The steps can further be sized to receive the engagement member 561 as it travels in the direction of expansion. Thus, each step 557 can define a seat against which the engagement member 561 can rest as it expands the cage 510 beyond the first or insertion configuration. As the engagement member 561 travels further in the expansion direction, the engagement member 561 can rest on successively spaced steps 557 in the expansion direction, thereby incrementally expanding and angulating the cage 510. The steps 557 and the flanges 566 can be spaced apart along the direction a suitable distance such that the engagement member 561 can rest against the steps 557 while the open end of the 572 of the sleeve 570 is disposed between adjacent flanges 566.

Figure 6:
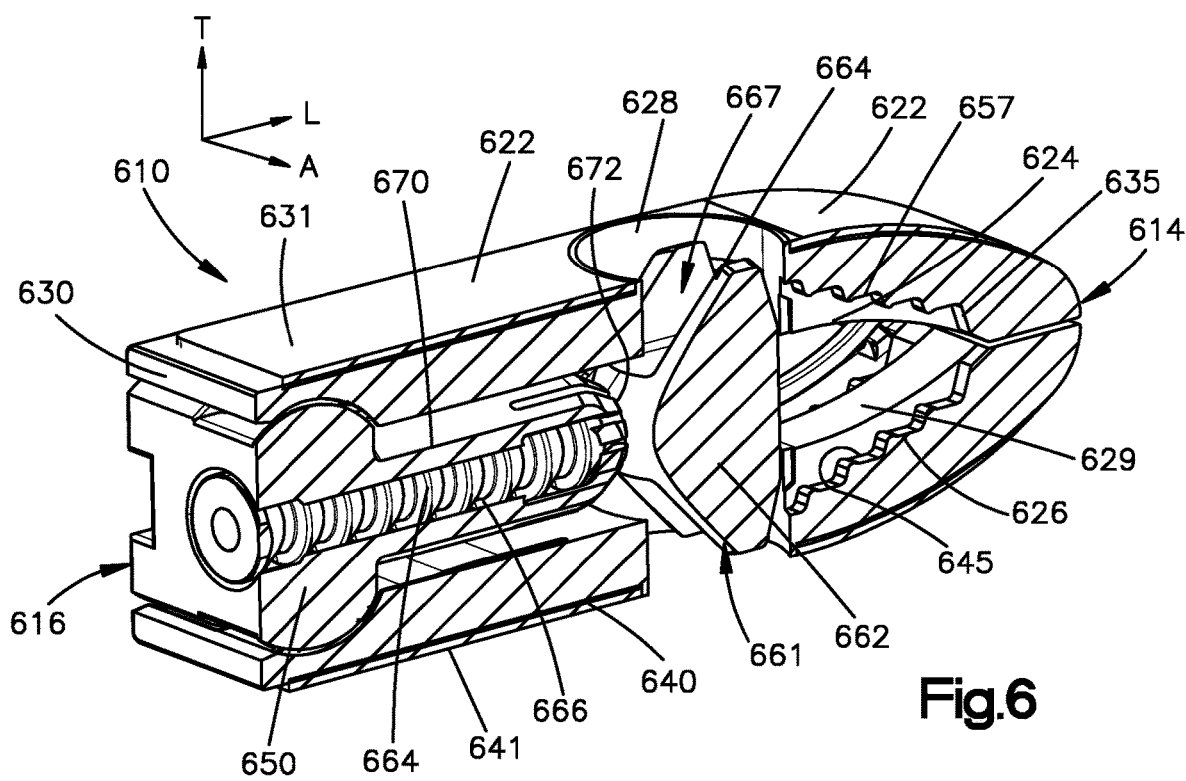
FIG. 6 is a cross-sectional perspective view of an intervertebral cage similar to the cage illustrated in FIG. 5, but including shallower porous structures.

FIG. 6 illustrates further still another example of an intervertebral cage of the present disclosure. As shown, the intervertebral cage 610 includes the features of the intervertebral cage 510. Thus, in FIG. 6, reference numerals corresponding to like elements of the cage 510 of FIG. 5 have been incremented by 100 for the purposes of clarity and convenience. As illustrated in FIG. 6, the porous structures 622 can have a reduced thickness with respect to the porous structures 522 illustrated in FIG. 5. Alternatively, the upper and lower bearing surfaces 631 and 641 can be devoid of the porous structures as described above with respect to FIG. 3.

As mentioned above, the intervertebral cages of the present disclosure are configured to be able to allow insertion through a narrow access path, but are able to be expanded and angularly adjusted so that the cages are capable of adjusting the angle of lordosis of the vertebral segments. By being able to angularly adjust and expand (or distract), the cages allow a very narrow anterior for insertion and a larger anterior after implantation to accommodate and adapt to larger angles of lordosis. Additionally, the cages can effectively restore sagittal balance and alignment of the spine, and can promote fusion to immobilize and stabilize the spinal segment.

With respect to the ability of the expandable cages to promote fusion, many in-vitro and in-vivo studies on bone healing and fusion have shown that porosity is necessary to allow vascularization, and that the desired infrastructure for promoting new bone growth should have a porous interconnected pore network with surface properties that are optimized for cell attachment, migration, proliferation and differentiation. At the same time, there are many who believe the implant's ability to provide adequate structural support or mechanical integrity for new cellular activity is the main factor to achieving clinical success, while others emphasize the role of porosity as the key feature. Regardless of the relative importance of one aspect in comparison to the other, what is clear is that both structural integrity to stabilize, as well as the porous structure to support cellular growth, are key components of proper and sustainable bone regrowth.

Accordingly, these cages may take advantage of current additive manufacturing techniques that allow for greater customization of the devices by creating a unitary body that may have both solid and porous features in one. In some embodiments as shown, the cages can have a porous structure, and be made with an engineered cellular structure that includes a network of pores, microstructures and nanostructures to facilitate osteosynthesis. For example, the engineered cellular structure can comprise an interconnected network of pores and other micro and nano sized structures that take on a mesh-like appearance. These engineered cellular structures can be provided by etching or blasting to change the surface of the device on the nano level. One type of etching process may utilize, for example, HF acid treatment. These same manufacturing techniques may be employed to provide these cages with an internal imaging marker. For example, these cages can also include internal imaging markers that allow the user to properly align the cage and generally facilitate insertion through visualization during navigation. The imaging marker shows up as a solid body amongst the mesh under x-ray, fluoroscopy or CT scan, for example. A cage may comprise a single marker, or a plurality of markers. These internal imaging markers greatly facilitate the ease and precision of implanting the cages, since it is possible to manufacture the cages with one or more internally embedded markers for improved visualization during navigation and implantation.

Another benefit provided by the implantable devices of the present disclosure is that they are able to be specifically customized to the patient's needs. Customization of the implantable devices is relevant to providing a preferred modulus matching between the implant device and the various qualities and types of bone being treated, such as for example, cortical versus cancellous, apophyseal versus central, and sclerotic versus osteopenic bone, each of which has its own different compression to structural failure data. Likewise, similar data can also be generated for various implant designs, such as for example, porous versus solid, trabecular versus non-trabecular, etc. Such data may be cadaveric, or computer finite element generated. Clinical correlation with, for example, DEXA data can also allow implantable devices to be designed specifically for use with sclerotic, normal, or osteopenic bone. Thus, the ability to provide customized implantable devices such as the ones provided herein allow the matching of the Elastic Modulus of Complex Structures (EMOCS), which enable implantable devices to be engineered to minimize mismatch, mitigate subsidence and optimize healing, thereby providing better clinical outcomes.

A variety of spinal implants may be provided by the present disclosure, including interbody fusion cages for use in either the cervical or lumbar region of the spine. Although only a posterior lumbar interbody fusion (PLIF) device is shown, it is contemplated that the same principles may be utilized in a cervical interbody fusion (CIF) device, a transforaminal lumbar interbody fusion (TLIF) device, anterior lumbar interbody fusion (ALIF) cages, lateral lumbar interbody fusion (LLIF) cages, and oblique lumbar interbody fusion (OLIF) cages.

Other embodiments of the disclosure will be apparent to those skilled in the art from consideration of the specification and practice of the disclosure provided herein. It is intended that the specification and examples be considered as exemplary only.

What is claimed is:

1. An expandable spinal implant, comprising:
    a housing comprising an upper plate configured for placement against an endplate of a first vertebral body, and a lower plate configured for placement against an endplate of a second, adjacent vertebral body, the housing defining a leading end with respect to insertion into an intervertebral space and a trailing end opposite the leading end, the leading end spaced from the trailing end in a forward direction, wherein the housing further comprises a sleeve having an opening configured to receive an insertion instrument, and teeth that extend from the sleeve in the forward direction; and
    an actuator configured to be moved by the insertion instrument relative to the upper and lower plates to effect angular adjustment of the spinal implant from an initial configuration to an expanded configuration, the actuator including one or more teeth configured to engage the plurality of teeth that extends from the sleeve to lock the spinal implant in the expanded configuration.

2. The expandable spinal implant of claim 1, wherein the actuator includes an enlarged head positioned between the sleeve and the leading end.

3. The expandable spinal implant of claim 2, wherein the enlarged head is configured to urge at least one of the upper and lower plates away from the other of the upper and lower plates.

4. The expandable implant of claim 2, wherein the enlarged head is configured to ride along a guide rail on at least one of the upper and lower plates.

5. The expandable implant of claim 1, wherein the actuator moves toward the leading end as the actuator moves relative to the upper and lower plates.

6. The expandable spinal implant of claim 1, wherein the upper and lower plates connect to the housing at a hinge.

7. The expandable spinal implant of claim 1, wherein the implant is configured for posterior lumbar interbody fusion.

8. The expandable spinal implant of claim 1, wherein the implant is configured for anterior lumbar interbody fusion.

9. The expandable spinal implant of claim 1, wherein the housing includes a porous surface.

10. The expandable spinal implant of claim 9, wherein the porous surface is on at least one of the upper and lower plates.

11. The expandable spinal implant of claim 1, wherein the leading end of the implant is tapered.

12. The expandable spinal implant of claim 1, wherein the housing further includes a bone graft window.

13. The expandable implant of claim 1, wherein the upper plate defines a respective pair of upper side walls that are spaced from each other so as to define an upper plate internal cavity therebetween, and the lower plate component defines a respective pair of lower side walls that are spaced from each other so as to define a lower plate internal cavity therebetween.

14. The expandable implant of claim 13, wherein the enlarged head is disposed within at least one of the upper plate internal cavity and the lower plate internal cavity.

15. The expandable implant of claim 1, wherein the upper plate defines an upper bearing surface, the lower plate defines a lower bearing surface, and angular adjustment of the spinal implant causes an angle defined between the upper and lower bearing surfaces to change.

* * * * *